(12) United States Patent
Vardi et al.

(10) Patent No.: US 6,596,020 B2
(45) Date of Patent: Jul. 22, 2003

(54) METHOD OF DELIVERING A STENT WITH A SIDE OPENING

(75) Inventors: Gil M. Vardi, Chesterfield, MO (US); Charles J. Davidson, Winnetka, IL (US); Eric Williams, Fairfield, CA (US)

(73) Assignee: Advanced Stent Technologies, Inc., Pleasanton, CA (US)

( * ) Notice: Subject to any disclaimer, the term of this patent is extended or adjusted under 35 U.S.C. 154(b) by 0 days.

(21) Appl. No.: 09/741,761

(22) Filed: Dec. 18, 2000

(65) Prior Publication Data

US 2001/0003161 A1 Jun. 7, 2001

Related U.S. Application Data

(60) Division of application No. 09/325,996, filed on Jun. 4, 1999, now abandoned, which is a continuation-in-part of application No. PCT/US99/00835, filed on Jan. 13, 1999, which is a continuation-in-part of application No. 09/007,265, filed on Jan. 14, 1998, now Pat. No. 6,210,429, which is a continuation-in-part of application No. 08/744,002, filed on Nov. 4, 1996, now abandoned.

(60) Provisional application No. 60/088,301, filed on Jun. 5, 1998.

(51) Int. Cl.[7] .................................................. A61F 2/06
(52) U.S. Cl. ........................ 623/1.11; 606/108; 604/264
(58) Field of Search ................................ 604/98, 98.01, 604/103.04, 101.04, 264, 523; 606/195, 108; 623/1.11

(56) References Cited

U.S. PATENT DOCUMENTS

| | | | |
|---|---|---|---|
| 1,596,754 A | 8/1926 | Moschelle | |
| 3,872,893 A | 3/1975 | Roberts | |
| 4,410,476 A | 10/1983 | Redding et al. | |
| 4,421,810 A | 12/1983 | Rasmussen | |
| 4,552,554 A | 11/1985 | Gould et al. | |
| 4,681,570 A | 7/1987 | Dalton | |
| 4,689,174 A | 8/1987 | Lupke | |
| 4,900,314 A | 2/1990 | Quackenbush | |
| 5,054,501 A | 10/1991 | Chuttani et al. | |
| 5,122,125 A | 6/1992 | Deuss | |
| 5,147,317 A | 9/1992 | Shank et al. | |
| 5,217,440 A | 6/1993 | Frassica | |
| 5,244,619 A | 9/1993 | Burnham | |
| 5,337,733 A | 8/1994 | Bauerfeind et al. | |
| 5,350,395 A | 9/1994 | Yock | |
| 5,404,887 A | 4/1995 | Prather | |
| 5,417,208 A | 5/1995 | Winkler | |
| 5,445,624 A | 8/1995 | Jiminez | |
| 5,458,605 A | 10/1995 | Klemm | |
| 5,489,271 A | 2/1996 | Andersen | |
| 5,496,292 A | 3/1996 | Burnham | |
| 5,669,932 A | 9/1997 | Fishell et al. | |
| 5,676,697 A | 10/1997 | McDonald | |
| 5,720,735 A | * 2/1998 | Dorros | ........................ 606/194 |

(List continued on next page.)

FOREIGN PATENT DOCUMENTS

WO      WO 92/19308      11/1992

OTHER PUBLICATIONS

SCIMED Life Systems, Inc.—TRIO™ 14 PTCA Catheter, *Re–engineering Over–the–Wire Balloon Technology*, Company Brochure, ©1994.

*Primary Examiner*—Paul Prebilic
(74) *Attorney, Agent, or Firm*—G. E. Ehrlich Ltd.

(57) ABSTRACT

A method of aligning a side opening in a primary stent in registry with the ostium of a branch vessel includes advancing a first guidewire through a primary vessel such that a distal end of the first guidewire extends past an intersection of the primary vessel and the branch vessel, advancing a catheter over the first guidewire to the intersection of the primary vessel and the branch vessel. A second guidewire is advanced out of the stent through the side opening and into the branch vessel.

5 Claims, 4 Drawing Sheets

U.S. PATENT DOCUMENTS

| | | | |
|---|---|---|---|
| 5,749,825 A | * | 5/1998 | Fischell et al. ................. 600/3 |
| 5,755,734 A | | 5/1998 | Richter et al. |
| 5,762,631 A | | 6/1998 | Klein |
| 5,851,464 A | | 12/1998 | Davila et al. |
| 6,096,073 A | * | 8/2000 | Webster et al. ............. 623/1.16 |
| 6,099,497 A | | 8/2000 | Adams et al. |
| 6,217,527 B1 | | 4/2001 | Selmon et al. |
| 6,221,080 B1 | | 4/2001 | Power |
| 6,231,563 B1 | | 5/2001 | White et al. |
| 6,261,273 B1 | * | 7/2001 | Ruiz ........................... 604/284 |
| 6,346,089 B1 | * | 2/2002 | Dibie ........................ 623/1.15 |
| 6,436,134 B2 | | 8/2002 | Richter et al. |
| 2002/0111675 A1 | | 8/2002 | Wilson |

\* cited by examiner

METHOD OF DELIVERING A STENT WITH A SIDE OPENING

CROSS-REFERENCES TO RELATED APPLICATIONS

The present application is a divisional of pending U.S. Application No. 09/325,996, filed on Jun. 4, 1999, which claims the benefit under 35 USC 119 of now expired U.S. Application No. 60/088,301, filed Jun. 5, 1998, and which also is a continuation-in-part of expired PCT Application No. US99/00835, filed Jan. 13, 1999, which is continuation-in-part of U.S. Application No. 09/007,265, filed Jan. 14, 1998, which issued on Apr. 3, 2001 as U.S. Pat. No. 6,210,429 and which is a continuation-in-part of U.S. Application No. 08/744,002 filed Nov. 4, 1996, now abandoned. U.S Application No. 09/325,996, of which the present application is a divisional, is also a continuation-in-part of U.S. Application No. 08/935,383, now abandoned, which is a divisional of U.S. Application No. 08/744,002, now abandoned, all of which are incorporated herein by reference in their entireties.

TECHNICAL FIELD

The present invention relates to catheter systems for delivering stents.

BACKGROUND OF THE INVENTION

A type of endoprosthesis device, commonly referred to as a stent, may be placed or implanted within a vein, artery or other tubular body organ for treating occlusions, stenoses, or aneurysms of a vessel by reinforcing the wall of the vessel or by expanding the vessel. Stents have been used to treat dissections in blood vessel walls caused by balloon angioplasty of the coronary arteries as well as peripheral arteries and to improve angioplasty results by preventing elastic recoil and remodeling of the vessel wall. Two randomized multicenter trials have recently shown a lower restenosis rate in stent treated coronary arteries compared with balloon angioplasty alone (Serruys, P W et al. New England Journal of Medicine 331: 489–495, 1994, Fischman, D L et al. New England Journal of Medicine 331:496–501, 1994). Stents have been successfully implanted in the urinary tract, the bile duct, the esophagus and the tracheo-bronchial tree to reinforce those body organs, as well as implanted into the neurovascular, peripheral vascular, coronary, cardiac, and renal systems, among others. The term "stent" as used in this Application is a device which is intraluminally implanted within bodily vessels to reinforce collapsing, dissected, partially occluded, weakened, diseased or abnormally dilated or small segments of a vessel wall.

One of the drawbacks of conventional stents is that they are generally produced in a straight tubular configuration. The use of such stents to treat diseased vessels at or near a bifurcation (branch point) of a vessel may create a risk of compromising the degree of patency of the primary vessel and/or its branches, or the bifurcation point and also limits the ability to insert a branch stent into the side branch if the result of treatment of the primary, or main, vessel is suboptimal. Suboptimal results may occur as a result of several mechanisms, such as displacing diseased tissue, plaque shifting, vessel spasm, dissection with or without intimal flaps, thrombosis, and embolism.

As described in related copending U.S. patent application Nos. 08/744,022, filed Nov. 4, 1996, now abandoned; 09/007,265, filed Jan. 14, 1998; 08/935,383, filed Sep. 23, 1997; and 60/088,301, filed Jun. 5, 1998; and PCT Patent Application WO 99/00835, filed Jan. 14, 1998; systems have been developed for deploying a primary stent in a primary vessel at the intersection of a primary vessel and a branch vessel with a branch stent extending into a branch vessel through a side opening in the primary stent. Unfortunately, several difficulties exist when attempting to position such an arrangement of a primary and branch stents at a vessel intersection.

For example, the insertion of separate guidewires into both the primary vessel and the secondary vessel is required before positioning a primary stent in a primary vessel with a branch stent projecting through a side opening in the primary stent into a branch vessel. Primary and branch stents are then advanced over the separate guidewires which have been pre-guided one after another into the respective primary and branch vessels, such that the primary stent can be deployed within the primary vessel and the branch stent can be deployed through the side opening in the primary stent into the branch vessel. Unfortunately, when attempting to guide two such separate guidewires through the primary vessel such that one enters the branch vessel, the two guidewires typically tend to wrap around one another and become entangled. Additionally, time and effort is required to individually position each of the two guidewires one after another.

An additional disadvantage of conventional stents is the difficulty in visualizing the stents during and after deployment, and in general, the fact that they are not readily imaged by low-cost and easy methods, such as x-ray or ultrasound imaging.

SUMMARY OF THE INVENTION

The present invention comprises a dual lumen catheter system having a guidewire received through the first lumen. A side sheath, (or alternatively, a second catheter), is slidably receivable within the second lumen of the dual lumen catheter. As will be explained, an advantage of the present dual lumen catheter system is that it may be used for deploying a primary stent in a primary vessel and a branch stent in a branch vessel, wherein the branch stent is deployed through an opening in the side of the primary stent with the side opening being in registry with the ostium of the branch vessel. An advantage of the present dual lumen catheter system is that it avoids having to separately position first and second guidewires within the respective primary and branch vessels prior to deployment of primary and branch stents thereover. Rather, with the present invention, only a single guidewire needs to initially be placed within the primary vessel, with the present dual lumen catheter system subsequently deploying both the primary and branch stents thereover.

The present invention also sets forth methods for aligning a side opening of a primary stent in registry with the ostium of a branch vessel using the present dual lumen catheter system. In a preferred aspect of the method, a first guidewire is positioned within the primary vessel such that a distal end of the first guidewire extends past a intersection of the primary vessel and the branch vessel. A primary stent is then advanced over the guidewire with the dual lumen catheter, wherein the first guidewire is received within a first lumen of the first catheter. The second lumen of the dual lumen catheter may preferably be formed by attaching a side portion to the dual lumen catheter.

The second lumen of the dual lumen catheter is preferably formed from polyamide and lubricated on its inner surface with graphite particles to make its interior surface microscopically rough thereby reducing sliding friction when a side sheath or second catheter is passed therethrough. Accordingly, the distal end of the side sheath, (which is received through the second lumen of the dual lumen catheter), can easily be slidably positioned to a desired location at the intersection of the primary and branch vessels such that the dual lumen catheter can be positioned at a desired location to deploy the primary stent within the primary vessel. After the distal end of the side sheath is positioned at the vessel intersection, a second guidewire can then be advanced through the side sheath to pass out of the distal end of the side sheath, (passing through the side opening in the primary stent and into the branch vessel), thereby aligning the side opening of the primary stent in registry with the ostium of the branch vessel. Thereafter, the primary stent may be deployed within the primary vessel, such as by inflating a first balloon disposed over the first guidewire at a distal end of the dual lumen catheter.

The present invention also comprises a method of delivering primary and branch stents into the intersection of a primary vessel and a branch vessel such that a side opening in the primary stent is positioned in registry with the ostium of the branch vessel, and such that the branch stent extends through the side opening in the primary stent and into the branch vessel. In a preferred aspect, this is accomplished by deploying a primary stent within the primary vessel such that a side opening in the primary stent is registry with the ostium of the branch vessel with a second guidewire passing out through the side opening in the primary stent and into the branch vessel as described above. A branch stent is then subsequently advanced over the second guidewire and into the branch vessel such that the branch stent passes out through the side opening in the primary stent and into the branch vessel. The primary stent may optionally include radially expandable portions which protrude outwardly from the side opening in the primary stent and into the walls of the branch vessel, holding the side opening in registry with the ostium of the branch vessel.

To deploy the branch stent, the side sheath can be removed from the second lumen of the dual lumen catheter leaving the second guidewire in position in the branch vessel. In addition, the entire catheter system can be removed leaving the two guidewires in place such that the second catheter can be advanced over the second guidewire and into the branch vessel. As such, the second catheter can then be advanced over the second guide wire with its distal end extending into the branch vessel. A second balloon disposed over the second guidewire at a distal end of the second catheter can then be used to deploy the branch stent within the branch vessel. The branch stent may optionally comprise a contact portion at its proximal end to secure the proximal end of the branch stent to the side opening in the primary stent.

In preferred aspects of the present invention, the distal end of the side sheath is positioned at the intersection of the primary vessel and the branch vessel by viewing its position under fluoroscopy. Also, in preferred aspects, the second guidewire is inserted through the side sheath and into the branch vessel under fluoroscopic viewing.

The present invention also comprises an apparatus for aligning a side opening in a primary stent in registry with the ostium of the branch vessel, comprising a dual lumen catheter system in which a first guidewire is slidably received within a first lumen in the catheter and a side sheath is slidably received within the second lumen of the dual lumen catheter. A second guidewire is slidably received within the lumen of the side sheath. To assist in guiding the second guidewire into the branch vessel, the side sheath may preferably taper to a narrow distal end, which may be curved slightly outwardly and which preferably comprises tungsten or other suitable radiopaque material such that it may be fluoroscopically viewed. In other preferred aspects, a first balloon is disposed over the first guidewire at a distal end of the dual lumen catheter and a second balloon is disposed over the second guidewire at a distal end of a second catheter which can be received within the second lumen of the dual lumen catheter.

Applications of the present system include the cardiac, coronary, renal, peripheral vascular, gastrointestinal, pulmonary, urinary and neurovascular systems and the brain. Further advantages of the present dual lumen catheter system are that it provides an improved stent delivery apparatus, which may deliver primary and branch stents to: 1) completely cover the bifurcation point of bifurcation vessels; 2) be used to treat lesions in one branch of a bifurcation while preserving access to the other branch for future treatment; 3) allow for differential sizing of the stents in a bifurcated stent apparatus even after a primary stent is implanted; 4) treat bifurcation lesions in a bifurcated vessel where the branch vessel extends from the side of the primary vessel; and 5) be marked with, or at least partly constructed of, material which is imageable by commonly used intraluminal catheterization visualization techniques including but not limited to ultrasound or x-ray.

DESCRIPTION OF THE SPECIFIC EMBODIMENTS

The present invention comprises methods of aligning a side opening in a primary stent in registry of the ostium of a branch vessel and methods for delivering primary and branch stents into an intersection of primary vessel and a branch vessel, such that the side opening in the primary stent is in registry with the ostium of the branch vessel with the branch stent extending through the side opening of the primary stent and into the branch vessel.

A novel catheter system is provided for accomplishing the preferred methods. The present catheter system comprises a dual lumen catheter having a guidewire received through its first lumen. In one aspect of the invention, a side sheath is slidably received through the second lumen of the dual lumen catheter. A second guidewire is received through the side sheath and the side sheath is positionable so as to align a side hole in a primary stent with a branch vessel.

In an alternative aspect, a second catheter is slidably received through the second lumen of the dual lumen catheter. The second catheter may optionally have a balloon disposed thereon such that first and second balloons are disposed over the dual lumen and second guidewires at the distal ends of the respective dual lumen and second catheters, for deploying the primary and branch stents respectively.

Figure 1:
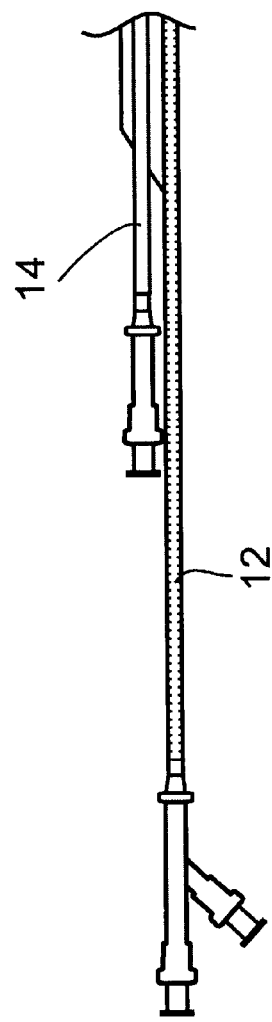
FIG. 1. is an illustration of a dual lumen catheter having a side sheath slidably received within a second lumen of the dual lumen catheter.

Referring to FIG. 1, a catheter system 10 is provided comprising a dual lumen catheter 12 and a side sheath 14, wherein side sheath 14 is slidably received within lumen 15 which may be formed as an extending side portion of catheter 12 such that side sheath 14 can be axially displaced with respect to catheter 12. The interior of lumen 15 is preferably lubricated to reduce sliding friction with side sheath 14. In a preferred aspect, the extending side portion of catheter 12 forming lumen 15 is fabricated of polyamide with graphite particles imbedded therein to yield a microscopically rough surface. Alternatively, the inner surface of lumen 15 may have metal powders, glass beads, Teflon powder or other inorganic fillers imbedded therein.

As will be explained, an advantage of the present dual lumen catheter 12 is that catheter 12 can be positioned at a desired location so as to align side hole 27 of primary stent 25 at the ostium of a branch vessel by positioning the distal end 16 of side sheath 14 at the ostium of the branch vessel. Specifically, in a preferred aspect method of using the present system, dual lumen catheter 12 can be positioned proximal the intersection of the primary and branch vessels to deploy a primary stent in the primary vessel with side sheath 14 positioned at the vessel intersection to deploy a second guidewire passing out through a side hole in a primary stent and into the branch vessel such that only one guidewire needs to initially be positioned within the primary vessel prior to subsequent deployment of the primary and branch stents.

Figure 2:
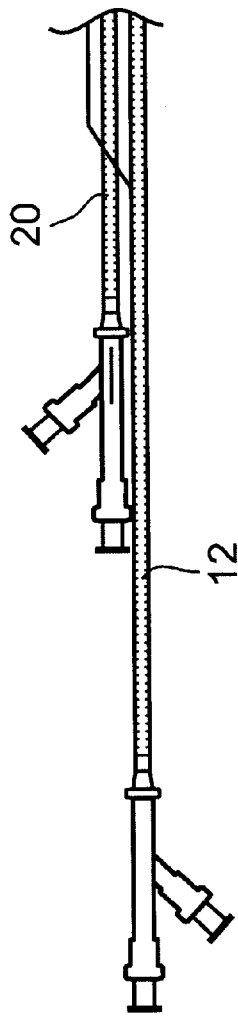
FIG. 2. is an illustration of a dual lumen catheter having a second catheter slidably received within a second lumen of the dual lumen catheter, with balloons positioned on the distal ends of both of the dual lumen catheter and the second catheter.
Figure 7:
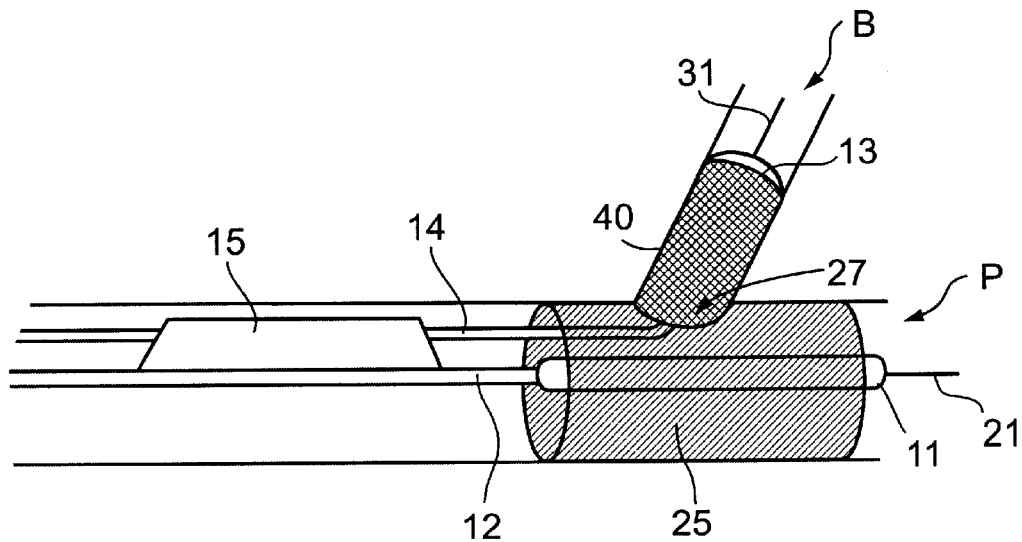
FIG. 7 is an illustration of the deployment of the branch stent by a second balloon disposed over the second guidewire.

As can be seen in FIG. 2, a second catheter 20 can be received in lumen 15. A balloon 11 disposed at the distal end of dual lumen catheter 10 may be used to deploy a primary stent in a primary vessel. In this aspect of the invention, side sheath 14 is preferably withdrawn over guidewire 31 after guide wire 31 is positioned in the branch vessel (FIG. 7). The second catheter 20 having a balloon 13 disposed at its distal end is then advanced over guide wire 31 with balloon 13 deploying an optional branch stent 40 as will be explained.

In a preferred aspect, the present invention is directed to aligning a side hole in a primary stent to a position in registry with the ostium of a branch vessel. This first aspect of the invention is illustrated in the sequential steps shown in FIGS. 3 to 5.

In another preferred aspect, the present invention is directed to deploying a branch stent in a branch vessel with the branch stent extending into the branch vessel through a side opening in the primary stent. This second aspect of the present invention is illustrated in the sequential steps shown in FIGS. 6 and 7. (The sequential steps shown in FIGS. 6 and 7 are accomplished after the sequential steps shown in FIGS. 3 to 5).

Figure 3:
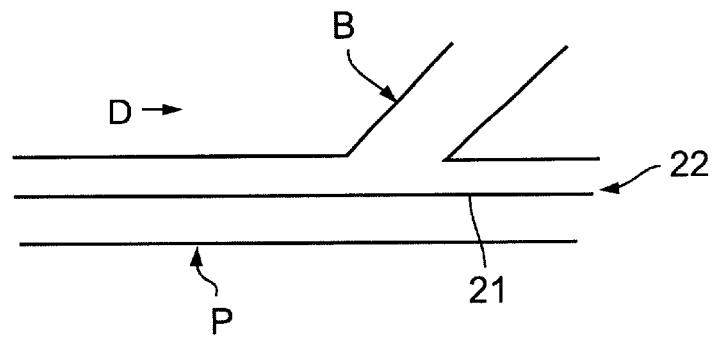
FIG. 3 is an illustration of a placement of first guidewire within a primary vessel.

Referring first to FIG. 3, a first guidewire 21 is advanced through a primary vessel P in direction D such that distal end 22 of guidewire 21 extends past the intersection of a primary vessel P and a branch vessel B.

Figure 4:
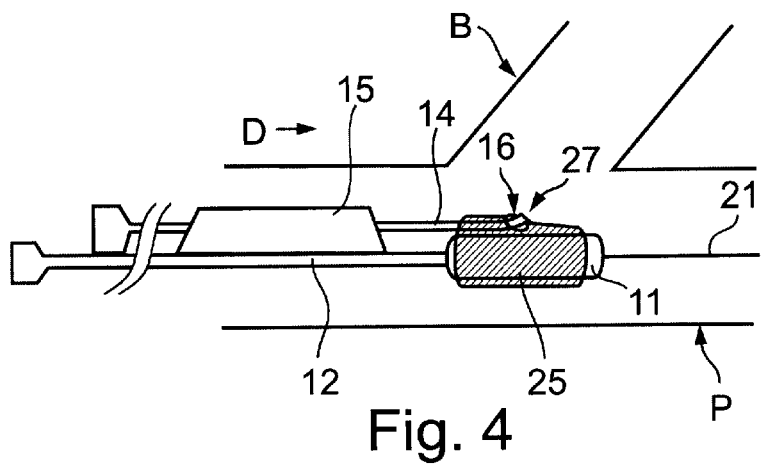
FIG. 4 is an illustration of the dual lumen catheter and side sheath advanced over the first guidewire to a position where the side opening in the primary stent is adjacent with the mouth of the branch vessel.

As shown in FIG. 4, dual lumen catheter 12 is then advanced in direction D over guidewire 21 such that a primary stent 25, (which is supported at a distal end of catheter 10, as shown), is oriented such that side hole 27 of stent 25 is positioned generally adjacent the mouth of branch vessel B. (Guidewire 21 is received within a lumen in catheter 10.) As can be seen, stent 25 is preferably crimped down onto side sheath 14, as shown. Preferably, distal end 16 of catheter 14 has tungsten, or other suitable radiopaque material, deposited thereon such that it can be viewed and positioned fluoroscopically. Preferably, stent 25 is initially crimped onto balloon 11 with distal end 16 of side sheath 16 projecting outwardly through side opening 27 as shown. As such, fluoroscopic positioning of distal end 16 aligns side opening 27 to branch vessel B, as dual lumen catheter 20 supporting stent 25 and side sheath 14 initially move together when stent 25 is initially crimped onto balloon 11.

Figure 5:
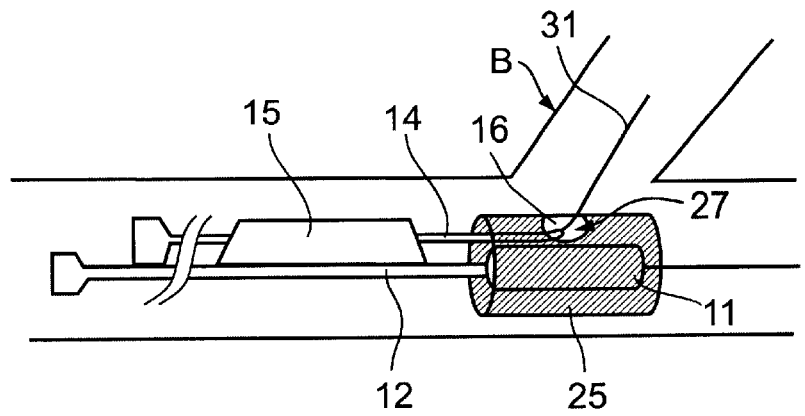
FIG. 5 is an illustration of the second guidewire as it is advanced out of the distal end of the side sheath, through the side opening in the primary stent and into the branch vessel.
Figure 6:
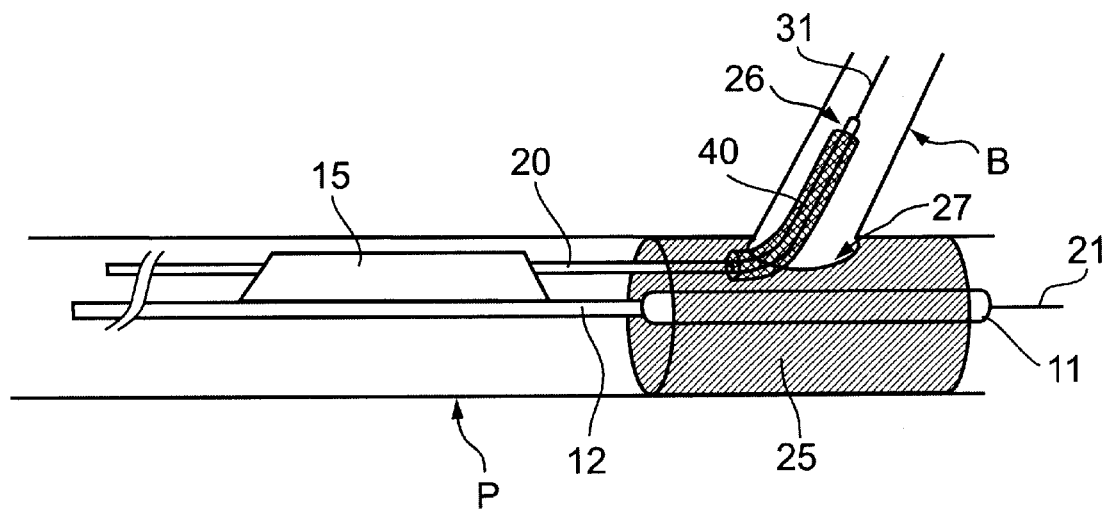
FIG. 6 is an illustration of a branch stent of advanced over the second guidewire and through the side opening in the primary stent and into the branch vessel by a second catheter received within the second lumen of the dual lumen catheter.

As shown in FIG. 5, after distal end 16 of catheter 14 is positioned as shown, a second guidewire 31 can then be advanced out of distal end 16 of side sheath 14, passing through side opening 27 in stent 25 and into branch vessel B. As also shown in FIG. 5, balloon 11 may be partially or fully inflated expanding stent 25 so as to provide an access space for a distal end 26 of second catheter 20 to be advanced therethrough, as will be explained.

Figure 9:
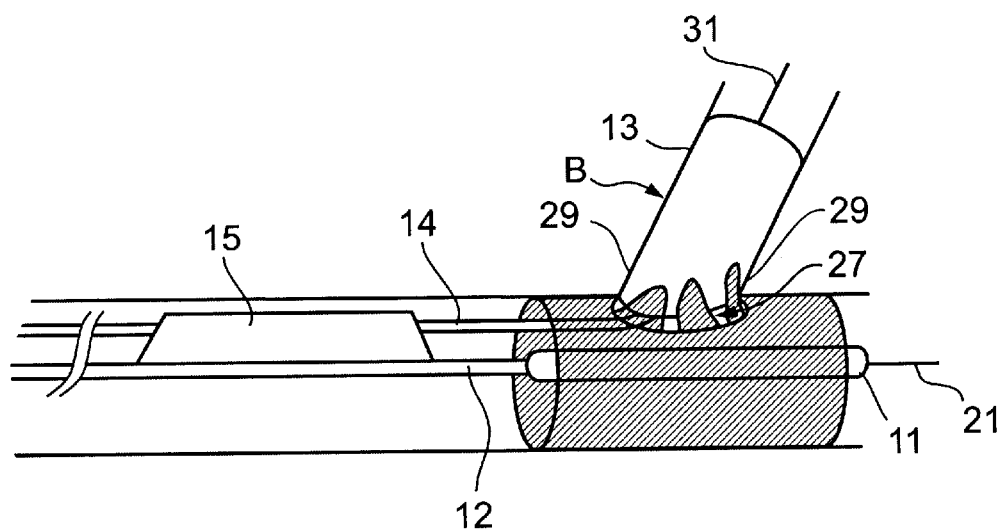
FIG. 9 shows an embodiment of the present invention with radially expandable portions around the side opening on the primary stent.

As shown in the optional step of FIG. 9, balloon 13 on catheter 14 can then be inflated to deploy radially expandable portions 29 extending laterally outward from the edges of side opening 27, such that portions 29 are pushed against the walls of branch vessel B, such that side opening 27 is positioned in registry with the ostium of branch vessel B. Further description of such radially expandable portions 29 which extend laterally outward from the edges of side opening 27 is set forth in Published PCT Patent Application WO 99/00835, filed Jan. 14, 1998, incorporated herein by reference in its entirety.

In a second aspect of the present invention, additional sequential steps, as illustrated in FIGS. 6 and 7, are instead carried out after the steps illustrated in FIGS. 3 to 5 to deploy a branch stent in a branch vessel with the branch stent extending through a side opening in the primary stent.

FIG. 6 is similar to FIG. 5, but side sheath 14 has been removed and a second catheter 20 has been advanced over guidewire 31 with a branch stent 40 disposed at distal end 26 of catheter 20. As shown in FIG. 6, distal end 26 of catheter 20 can be advanced over guidewire 31 such that stent 40 is advanced through side hole 27 in stent 25 and is positioned in branch vessel B.

As shown in FIG. 7, stent 40 can then be fully deployed within branch vessel B by inflating second balloon 13 disposed at distal end 26 of catheter 20.

Primary stent 25 can be fully deployed by inflation of balloon 11 either before, after or concurrently with branch stent 40 being deployed by inflation of balloon 13.

Figure 8:
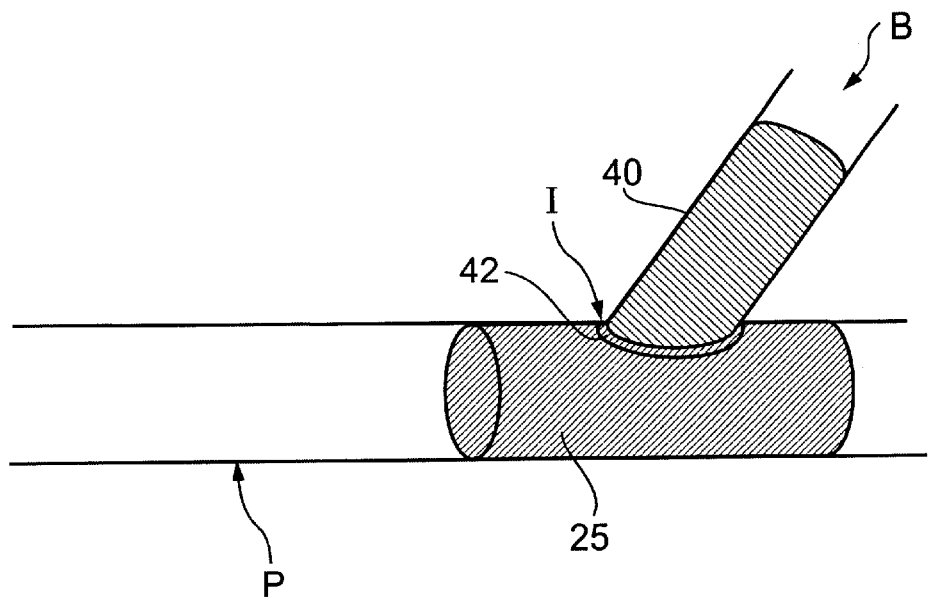
FIG. 8 is an illustration of the fully deployed primary and branch stents with the guidewires and dual lumen catheter removed.

Lastly, as can be seen in FIG. 8, catheter system 10, (comprising catheter 12, catheter 20, and guidewires 21 and 31) can be removed after deployment of stents 25 and 40, leaving a bifurcated support at the intersection of primary vessel P and branch vessel B as shown.

As can also be seen, stent 40 may further comprise a contact portion 42 which remains disposed within side opening 27 thereby securing the proximal end of stent 40 to side opening 27 of stent 25, thereby providing a bifurcated stent arrangement covering vessel intersection I.

What is claimed is:

1. A method of delivering a stent having a side opening configured to be aligned with the ostium of a branch vessel, comprising:

advancing a first guidewire through a primary vessel such that a distal end of the first guidewire extends past an intersection of the primary vessel and the branch vessel;

advancing a catheter over the first guidewire to the intersection of the primary vessel and the branch vessel, the catheter comprising a catheter body having a proximal end, a distal end, a first guidewire lumen extending between the proximal end and the distal end through which the first guidewire passes, and a stent having a side opening disposed over the catheter, and a side sheath coupled to the catheter body and the stent, the side sheath having a second guidewire lumen; and thereafter advancing a second guidewire through the second guidewire lumen of the side sheath such that the second guidewire passes through the side opening in the stent and into the branch vessel.

2. The method of claim 1, further comprising:

deploying the stent within the primary vessel by inflating a balloon disposed on the catheter.

3. The method of claim 1, further comprising viewing the position of the distal end of the side sheath under fluoroscopy.

4. The method of claim 2, further comprising:

inflating a second balloon disposed on the side sheath.

5. The method of claim 2, further comprising retracting the catheter and the side sheath, and advancing a branch stent over the second guidewire, through the side opening the stent into the branch vessel.

* * * * *